United States Patent [19]

Takeda et al.

[11] Patent Number: 5,075,476

[45] Date of Patent: Dec. 24, 1991

[54] PROCESS FOR PRODUCTION OF SULFONIUM COMPOUNDS AND NOVEL METHYLTHIPHENOL DERIVATIVES

[75] Inventors: Mutsuhiko Takeda; Isao Hagiwara; Fumiya Zaima; Shuzabu Sakaguchi, all of Tokyo, Japan

[73] Assignee: Mitsubishi Gas Chemical Company, Inc., Tokyo, Japan

[21] Appl. No.: 529,896

[22] Filed: May 29, 1990

[30] Foreign Application Priority Data

Jun. 7, 1989 [JP] Japan .................................. 1-143017
Jul. 20, 1989 [JP] Japan .................................. 1-188118

[51] Int. Cl.$^5$ ............................................. C07F 7/08
[52] U.S. Cl. .................................... 556/428; 558/20; 558/23; 558/271
[58] Field of Search .......................... 558/271, 20, 23; 556/428

[56] References Cited

FOREIGN PATENT DOCUMENTS 0210674 2/1987 European Pat. Off. ............. 558/271
0245662 11/1987 European Pat. Off. .
0346756 12/1989 European Pat. Off. .
0401696 12/1990 European Pat. Off. ............. 558/271
0290658 11/1989 Japan .................................. 558/271

OTHER PUBLICATIONS

H. M. Gilow et al., "Substituent Effects of Positive Poles in Aromatic Substitution. II. The Nitration of Sulfonium Salts", Aug. 1967, pp. 2580–2583, Journal of Organic Chemistry, vol. 32.
Chemical Abstracts, vol. 112, No. 25, Jun. 1990, Abstract No. 234992h.

*Primary Examiner*—Paul F. Shaver
*Attorney, Agent, or Firm*—Frishauf, Holtz, Goodman & Woodward

[57] ABSTRACT

Disclosed is process for producing a sulfonium compound of the general formula (III), comprising reacting alkylthiophenol derivative of the general formula (I) and dialkyl sulfate of the general formula (II) in the presence of at least one inorganic compound selected from the group consisting of alkali metal carbonate, alkali metal hydrogencarbonate, alkaline earth metal hydroxide, alkaline earth metal carbonate, and oxides of Group II metals of the Periodic Table.

General Formula (I):

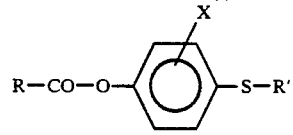

General Formula (II):
$(R^2)_2SO_4$

General Formula (III):

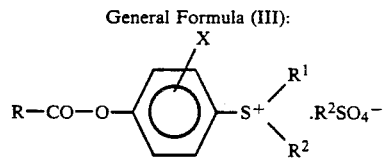

wherein all the symbols are as defined in the appended claims.

10 Claims, No Drawings

PROCESS FOR PRODUCTION OF SULFONIUM COMPOUNDS AND NOVEL METHYLTHIPHENOL DERIVATIVES

BACKGROUND OF THE INVENTION

1. Field of the Invention

The present invention relates to a process for production of sulfonium compounds and novel methylthiophenol derivatives. More particularly, it is concerned with a process for producing sulfonium compounds, dialkylsulfoniophenol derivatives represented by the general formula (III), by sulfoniumating alkylthiophenol derivatives represented by the general formula (I) with dialkyl sulfate represented by the general formula (II).

General Formula (I):

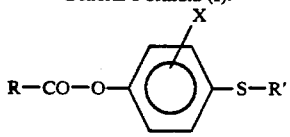

General Formula (II):
$(R^2)_2SO_4$

General Formula (III):

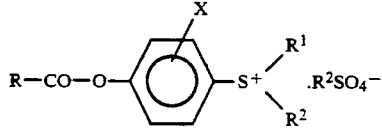

In the general formulas (I), (II) and (III), $R^1$ and $R^2$ may be identical or different and are each a lower alkyl group having 1 to 4 carbon atoms, and X is a hydrogen atom, a halogen atom, or a lower alkyl group having 1 to 4 carbon atoms.

In the general formulas (I) and (III), R is a tert-butyloxy group, a tert-amyloxy group, a p-methoxybenzyloxy group, a 2-(trimethylsilyl)ethoxy group, a 1-adamantyloxy group, a bornyloxy group, or an isobornyloxy group.

Sulfonium compounds represented by the general formula (III) are useful compounds as reagents for introduction of an acyl group as a protecting group to various compounds in the organic chemical field, e.g., synthesis of peptides, because they exhibit acylating action in an aqueous solution.

The term "acyl" as used herein refers to an atomic group derived by removal of a hydroxy group from a carbonic acid monoester.

The present invention further relates to novel methylthiophenol derivatives capable of being precursors for the above sulfonium compounds and more specifically to novel methylthiophenol derivatives represented by the general formula (I'):

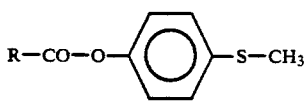

wherein R is the same as defined above.

2. Description of the Related Arts

For production of the sulfonium compounds represented by the general formula (III), a method of reacting acid halides, i.e., carbonylhalogenide compounds with p-dialkylsulfoniophenol alkylsulfate in the presence of a base has been generally employed.

Japanese Patent Application Laid-Open No. 8365/1988, for example, discloses a method in which acid chloride is used as the acid halide, and triethylamine is used as the base.

This method, however, is not necessarily satisfactory for practical use, because a complicated operation is required for separation and purification of the objective products, sulfonium compounds of the general formula (III), from by-products of triethylamine hydrochloride.

Moreover, in this method, the desired sulfonium compound cannot be obtained unless an unstable compound such as tert-butoxycarbonyl chloride or p-methoxybenzyloxycarbonyl chloride is used as the acid halide. In some cases, the desired product cannot be obtained at all. Thus the method is not desirable from an economic standpoint and is unsuitable for pracical use.

A method of converting thioanisole into the corresponding sulfonium with dimethyl sulfate is known (H. M. Gilow & G. L. Walker, J. Org. Chem., 32, 2580 (1967)).

When a p-methylthiophenol derivative, one of the alkylthiophenol derivatives of the general formula (I), is intended to be converted into the corresponding sulfonium compound with dimethyl sulfate, besides the desired sulfonium compound, a large amount of decomposition product, p-dimethylsulfoniophenol methylsulfate, is produced. Thus the yield of the desired sulfonium compound is low, and in some cases, the desired product is not obtained at all but only decomposition product is formed.

The present invention is intended to provide an industrially advatageous process for producing the desired sulfonium compound with high efficiency and at low production costs by reacting alkylthiophenol derivatives and dialkyl sulfate.

The present inventors made investigations on a method of synthesis of sulfonium compounds represented by the general formula (III) in order to overcome the above problems. As a result, it has been found that in the reaction of alkylthiophenol derivatives represented by the general formula (I) with dialkyl sulfate represented by the general formula (II), if the reaction is carried out in the presence of specified inorganic compounds, the decomposition reaction of the sulfonium compounds can be inhibited and the desired products can be obtained with high efficiency.

Moreover, in the course of the above investigations, it has been found that among the alkylthiophenol derivatives of the general formula (I) to be used as the starting material for the above reaction, specified compounds are novel compounds.

Based on the findings, the present invention has been accomplished.

SUMMARY OF THE INVENTION

An object of the present invention is to provide a process for efficiently producing the sulfonium compounds represented by the general formula (III).

Another object of the present invention is to provide a process for producing the above sulfonium compounds on industrial scale without use of complicated operations and in high yields.

Still another object of the present invention is to provide a novel methylthiophenol derivative (or methylthiophenyl carbonate).

The present invention relates to a process for producing sulfonium compounds represented by the general formula (III) which comprises reacting alkylthiophenol derivatives represented by the general formula (I) and dialkyl sulfate represented by the general formula (II) in the presence of at least one inorganic compound selected from alkali metal carbonate, alkali metal hydrogencarbonate, alkaline earth metal hydroxide, alkaline earth metal carbonate, and oxides of Group II metals of the Periodic Table.

The present invention relates also to a methylthiophenol derivative (or methylthiophenyl carbonate) represented by the general formula (I').

DESCRIPTION OF THE PREFERRED EMBODIMENTS

In the general formula (I), $R^1$ is a lower alkyl group having 1 to 4 carbon atoms, preferably a methyl group or an ethyl group. R is a tert-butyloxy group, a tert-amyloxy group, a p-methoxybenzyloxy group, a 2-(trimethylsilyl)ethoxy group, a 1-adamantyloxy group, a bornyloxy group, or a isobornyloxy group.

Specific examples of alkylthiophenol derivatives represented by the general formula (I) are tert-butyl p-methylthiophenyl carbonate, p-methoxybenzyl p-methylthiophenyl carbonate, tert-amyl p-methylthiophenyl carbonate, 2-(trimethylsilyl)ethyl p-methylthiophenyl carbonate, 1-adamantyl p-methylthiophenyl carbonate, bornyl p-methylthiophenyl carbonate, and isobornyl p-methylthiophenyl carbonate.

As dialkyl sulfates represented by the general formula (II), those in which $R^2$ is a lower alkyl group having 1 to 4 carbon atoms are preferred, and those in which $R^2$ is a methyl group or an ethyl group, and which are easily available are particularly suitable. X is appropriately chosen from a hydrogen atom, a halogen atom and an alkyl group, dependong on solubility, acylating reactivity, and so forth of the sulfonium compound of the general formula (III). In general, X is preferably a hydrogen atom. When X is an alkyl group, a lower alkyl group having 1 to 4 carbon atoms is preferred.

Preferred examples of the dialkyl sulfate represented by the general formula (II) are dimethyl sulfate and diethyl sulfate.

In accordance with the process of the present invention, an alkylthiophenol derivative represented by the general formula (I) and dialkyl sulfate represented by the general formula (II) are reacted with each other in the presence of a specified inorganic compound to convert the alkylthio group of the alkylthiophenol derivative into sulfonium, thereby synthesizing a sulfonium compound of the general formula (III).

One of the features of the present invention is that by-products which are difficult to separate from the desired product are not formed and, therefore, a complicated separation and purification operation after the reaction are substantially not required and the process is very economical.

The specified inorganic compound (hereinafter sometimes referred to merely as an "inorganic compound") to be used in the present invention includes alkali metal carbonate, alkali metal hydrogencarbonate, alkaline earth metal hydroxide, alkaline earth metal carbonate, and oxides of Group II metals of the Periodic Table.

Examples of the above inorganic compounds are sodium carbonate, potassium carbonate, sodium hydrogencarbonate, calcium hydroxide, calcium carbonate, calcium oxide, magnesium oxide, and zinc oxide. Of these compounds, sodium carbonate and calcium oxide are suitable. These inorganic compounds are preferably used in the form of anhydride, and powdery inorganic compounds are preferred. These compounds can be used in combination with each other.

The amount of the inorganic compound used is preferably 0.01 to 1 equivalent, particularly preferably 0.1 to 0.5 equivalent per equivalent of the dialkyl sulfate of the general formula (II). One equivalent as used herein is a value calculated with the dialkyl sulfate as a divalent acid. For example, in the case of sodium hydrogencarbonate, 2 mol of sodium hydrogencarbonate per 1 mol of the dialkyl sulfate is equal to one equivalent; in the case of potassium carbonate, 1 mol of potassium carbonate, to one equivalent; and in the case of calcium oxide, 1 mol of calcium oxide, to one equivalent.

In accordance with the process of the present invention, dialkyl sulfate is added to a mixture of an alkylthiophenol derivative represented by the general formula (I) (hereinafter sometimes referred to as "MSP compound") and the inorganic compound, and reacted with stirring while heating in the presence or the absence of a solvent.

The present invention, however, is not limited to the above process. For example, after heating of a mixture of the inorganic compound and MSP compound, dialkyl sulfate can be added thereto.

The amount of the dialkyl sulfate to be used is not limited as long as it is at least one mol per mol of MSP compound. From viewpoints of reaction time and yield, it is preferably 5 to 15 mol, particularly preferably 8 to 12 mol.

The solvent to be used in the present invention is not limited as long as it does not react with the MSP compound or dialkyl sulfate. For example, aprotic polar solvents such as acetonitrile, esters such as ethyl acetate, ethers such as dioxane, and aromatic hydrocarbons such as toluene can be used. Preferably aprotic polar solvents are used. Acetonitrile is one of solvents used more preferably. Two or more solvents can be used in combination with each other. Although the amount of the solvent used varies with the type of the solvent or the type of the MSP compound, in general, it is preferably 0.1 to 10 L (L=liter) per mol of the MSP compound. It is more preferably 0.5 to 3 L per mol of the MSP compound. Depending on the ratio of the MSP compound to the dialkyl sulfate, the reaction can be carried out without use of a solvent.

In the reaction of the present invention, when the reaction temperature is too low, the rate of reaction is small. On the other hand, as the reaction temperature is higher, the rate of reaction is larger. However, when the reaction temperature is too high, the sulfonium compound formed sometimes undergoes thermal decomposition depending on the type thereof. In general, therefore, the reaction temperature is preferably 30° to 80° C. and more preferably 50° to 70° C.

In the process of the present invention, after completion of the reaction, the inorganic compound is removed by filtration, and upon addition of a poor solvent such as ether or ethyl acetate to the filtrate, the desired sulfonium compound is obtained in the form of crystals or as an oily material. In the process of the present invention, since by-products which are difficult to separate are not formed, the desired product can be very easily separated and purified.

In accordance with the process of the present invention, the desired sulfonium compound can be easily isolated without complicated separations or purification operations, for removal of triethylamine hydrochloride as needed in the conventional methods, and moreover, only by adding a poor solvent to the reaction mixture, because p-dimethylsulfoniophenol methylsulfate resulting from decomposition of the product is not formed. According to the process of the present invention, the sulfonium compound of the general formula (III) is produced efficiently on an industrial scale and econominically.

The sulfonium compound has an ability to acylate an amino group of amino acid in an aqueous solution and thus is capable of becoming a highly useful protective reagent.

Among the alkylthiophenol derivatives of the above general formula (I), those in which $R^1$ is a methyl group and X is hydrogen, i,e., methylthiophenol derivatives represented by the general formula (I') are novel compounds. The methylthiophenol derivatives represented by the general formula (I') (hereinafter sometimes abbreviated as "Roc-MSP") can be easily synthesized by reacting p-methylthiophenyl chloroformate represented by the formula (IV) (hereinafter sometimes abbreviated as "CF-MSP") and alcohols represented by the formula (V) (hereinafter referred to merely as "alcohol") in the presence of pyridine in a dichloromethane solvent.

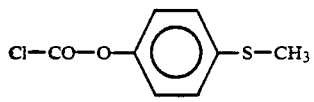

(IV)

R—OH (V)

In the present invention, the order of adding the above starting materials is not critical. In general, there is employed a method in which a solution of pyridine and alcohol in dichloromethane is dropped to a solution of CF-MSP in dichloromethane. The reaction temperature is suitably 0° to 40° C. The amount of dichloromethane used as a solvent is suitably 0.5 to 3 L per mol of CF-MSP.

After completion of the reaction, Roc-MSP can be obtained by washing the reaction solution with water to remove pyridine hydrochlorate and distilling away dichloromethane from the organic layer. By recrystalizing from methanol or hexane, if necessary, the desired Roc-MSP can be purified.

An advantage of using pyridine as a base in the present invention is that the desired product cannot be obtained at all when a base other than pyridine is used. For example, the present inventors have experienced that when triethylamine is used in the reaction of tert-amyl alcohol and p-methylthiophenyl chloroformate, the desired tert-amyl p-methylthiophenyl carbonate cannot be obtained at all.

CF-MSP to be used as the starting material for producing Roc-MSP is obtained by reacting phosgene and p-methylthiophenol represented by the general formula (VI) (hereinafter sometimes abbreviated as "MSP-OH") in the presence of pyridine as a base.

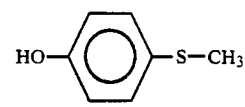

(VI)

A solution of MSP-OH and pyridine in dichloroformate is dropped to a dichloromethane solution containing 1.5 to 5 mol, preferably 2 to 3 mol of phosgene per mol of MSP-OH at a temperature of −30° to 10° C., preferably −20° to 0° C.

The amount of dichloromethane used as a solvent is preferably 0.1 to 10 L, more preferably 0.5 to 3 L per mol of MSP-OH.

After completion of the reaction, excessive phosgene and dichloromethane as a solvent are distilled away. To the residue, a solvent incapable of dissolving pyridine hydrochlorate, such as hexane or petroleum ether, is added to dissolve CF-MSP, and the pyridine hydrochlorate is separated by filtration. Upon distillation of the hexane from the filtrate, CF-MSP is obtained as a oily material. This CF-MSP can be purified by distilling under reduced pressure, if necessary.

An advantage of using pyridine as a base in the synthesis of CF-MSP is that the side reaction is decreased and the yield of CF-MSP is high. Another advantage is that since the same solvent and base are used in the subsequent reaction, synthesis of Roc-MSP, the subsequent reaction can be carried out as such without isolation of CF-MSP. That is, by supplementing a solvent to the reaction solution of CF-MSP from which excessive phosgene has been distilled away along with the solvent, and dropping alcohol and pyridine, the reaction can be continued to the synthesis of Roc-MSP without an isolation operation of CF-MSP.

Roc-MSP as obtained above is a stable substance and is free from any problems even if stored at room temperature for several months. Roc-MSP can be used as a protective reagent by sulfoniumating or sulfonylating through oxidation depending on the type of amino acid to be protected.

By carrying out the process for production of sulfonium compounds according to the present invention, the desired sulfonium compounds of the general formula (III) can be produced with high efficiency.

The present invention is described in greater detail with reference to the following examples.

EXAMPLE 1

(Preparation of Chloroformate)

Six hundred ml of dichloromethane was placed in a flask, and 64 ml (99 g, 1.0 mol) of phosgene was introduced thereto while cooling with ice. To the resulting solution, 100 ml of a dichloromethane solution containing 39.55 g (0.5 mol) of pyridine and 70.10 g (0.5 mol) of p-mehtylthiophenol was dropped while maintaining the reaction temperature at less than 5° C. After completion of the dropwise addition, the resulting mixture was stirred for one hour while cooling with ice. Then, a distillation apparatus was attached to the flask, which was then heated on a hot water bath maintained at 50° C. to distill away excessive phosgene and part of the solvent. Finally, the remaining solvent was removed under reduced pressure. Then, 700 ml of hexane was added to the residue as obtained above and stirred at room temperature for one hour. Pyridine hydrochlorate precipitated was removed by filtration, and the filtrate was concentrated by the use of an evaporator. Finally the hexane was completely removed in vacuum whereupon 101.5 g of crude p-methylthiophenyl chloroformate was obtained as an oily material.

The purity as determined based on the chlorine content and a high-performance liquid chromatographic analysis was 96.6%. A main impurity contained in the product was residual hexane, and the amount of bis p-methylthiophenyl carbonate was only less than 0.4%.

Upon purification of the crude p-methylthiophenyl chloroformate by distillation under reduced pressure, 86.02 g of pure p-methylthiophenyl chloroformate was obtained (yield 85%).

Boiling point: 96.0°-98.5° C. (0.3 mmHg)

$^1$H-NMR (CDCl$_3$): δ=2.38 (3H, s, S-Me) (Me:-methyl), 6.95-7.40 (4H, m,

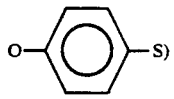

IR (NaCl): 1790 cm$^{-1}$ (C=O)
Elemental Analysis

|   | Calculated | Found  |
|---|------------|--------|
| C | 47.41%     | 47.48% |
| H | 3.48%      | 3.31%  |
| Cl| 17.49%     | 17.36% |

EXAMPLE 2

(Preparation of Carbonate)

One hundred ml of dichloromethane and 20.27 g (0.1 mol) of p-methylthiophenyl chloroformate prepared in the same manner as in Example 1 were placed in a flask, and 50 ml of a dichloromethane solution containing 8.15 g (0.1 mol) of tert-amyl alcohol and 8.70 g (0.11 mol) of pyridine was dropped thereto at room temperature. The resulting mixture was then stirred for two hours. The reaction solution was washed with water to remove pyridine hydrochlorate, and the organic layer was concentrated under reduced pressure. Finally excessive pyridine was removed in vacuum whereupon 5.09 g of the desired product, tert-amyl p-methylthiophenyl carbonate was obtained as an oily material (yield 100%).

$^1$H-NMR (CDCl$_3$): δ=0.97 (3H, t, J=7Hz, t-Am) (Am:amyl), 1.52 (6H, s, t-Am), 1.87 (2H, q, J=7Hz, t-Am), 2.42 (3H, s, S-Me), 6.95-7.40 (4H, m,

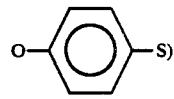

IR (NaCl): 1755 cm$^{-1}$ (C=O)
Elemental Analysis

|   | Calculated | Found  |
|---|------------|--------|
| C | 61.39%     | 61.05% |
| H | 7.13%      | 7.28%  |

COMPARATIVE EXAMPLE 1

The procedure of Example 2 was repeated with the exception that triethylamine was used in place of pyridine.

The desired product, tert-amyl p-methylthiophenyl carbonate was not obtained at all, and a substance supposed a reaction product of p-methylthiophenyl chloroformate and triethylamine was obtained.

EXAMPLES 3 TO 5

The procedure of Example 2 was repeated with the exception that alcohol as shown in Table 1 was used in place of tert-amyl alcohol.

When the reaction product was crystalline, it was purified by recrystallizing from methanol.

The results are shown in Table 1, and physical values of each substance are shown in Table 2.

TABLE 1

| Example   | Alcohol                        | Product (Roc-MSP)                                                      | Yield (%) | Substance No. |
|-----------|--------------------------------|------------------------------------------------------------------------|-----------|---------------|
| Example 3 | 1-Adamantanol                  | 1-Adamantyl p-methyl thiophenyl carbonate                              | 94        | (3)           |
| Example 4 | Borneol/Isoborneol (80/20 mixture) | Bornyl p-methylthiophenyl carbonate (containing 20% of isobornyl isomer) | 100       | (4)           |
| Example 5 | 2-(Trimethylsilyl)ethanol      | 2-(Trimethylsilyl)ethyl p-mehtylthiophenyl carbonate                   | 95        | (5)           |

TABLE 2

(Physical Values of Roc-MSR)

| Substance No. | m.p. (°C.) | IR | $^1$H-NMR(CDCl$_3$) | Elemental Analysis Calculated | Found |
|---|---|---|---|---|---|
| Substance 3 | 73.0-74.0 | (KBr) 1745 cm$^{-1}$ (C=O) | δ = 1.69(6H, s(broad), adamantyl) 2.19(9H, s(broad), adamantyl) 2.43(3H, s, S—Me) | C: 67.89% H: 6.96% | 67.51% 7.01% |

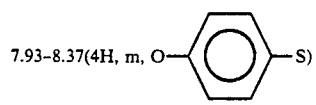

7.93-8.37(4H, m,

TABLE 2-continued (Physical Values of Roc-MSR)

| Substance No. | m.p. (°C.) | IR | $^1$H-NMR(CDCl$_3$) | Elemental Analysis Calculated | Found |
|---|---|---|---|---|---|
| Substance 4 | Oily | (NaCl) 1755 cm$^{-1}$ (C=O) | δ = 0.92(9H, s, CH$_3$—C in bornyl) <br><br> 1.15–2.80(7H, m, bornyl) <br> 2.41(3H, m, S—Me) <br><br> 4.50–5.10(1H, m, CH—O) <br><br> (4.50–4.70: isobornyl) <br> (4.70–5.10: bornyl) <br><br> 6.98–7.40(4H, m, O—⟨C$_6$H$_4$⟩—S) | C: 67.47% <br> H: 7.55% | 67.03% <br> 7.50% |
| Substance 5 | 37.0–38.5 | (KBr) 1760 cm$^{-1}$ (C=O) | δ = 0.03(9H, s, Me$_3$Si) <br> 0.09–1.25(2H, m, Si—CH$_2$) <br> 2.45(3H, s, S—Me) <br> 4.11–4.49(2H, m, CH$_2$—O) <br><br> 7.00–7.42(4H, m, O—⟨C$_6$H$_4$⟩—S) | C: 54.89% <br> H: 7.09% | 54.72% <br> 7.04% |

EXAMPLE 6

Six hundred ml of dichloromethane was placed in a flask, and 64 ml (99 g, 1.0 mol) of phosgene was introduced thereto while cooling with ice. To the solution thus obtained, a solution of 39.55 g (0.5 mol) of pyridine and 70.10 g (0.5 mol) of p-mehtylthiophenol in 100 ml of dichloromethane was dropped in such a manner that the reaction temperature did not exceed 5° C. After completion of dropwise addition, the resulting mixture was stirred for one hour while cooling with ice. Then, a distillation apparatus was attached to the flask, and excessive phosgene and part of the solvent were distilled away by heating with a water bath maintained at 50° C.

When the amount of distillate reached about 500 ml, heating was stopped. In this way, a solution of p-methylthiophenyl chloroformate was obtained.

To this solution, 500 ml of dichloromethane was added, and the resulting mixture was again cooled with ice. Then, a solution of 17.79 g (0.6 mol) of tert-butyl alcohol and 47.46 g (0.6 mol) of pyridine in 100 ml of dichloromethane was dropped. After completion of dropwise addition, the resulting mixture was stirred at room temperature for 3 hours.

After completion of the reaction, the reaction solution was washed three times with water to remove pyridine hydrochlorate, and the organic layer was dried over sodium sulfate.

Dichloromethane, unreacted tert-butyl alcohol, and pyridine were distilled away from the organic layer in vacuum. To the residue thus obtained, methanol was added. On allowing the resulting mixture to stand in a refrigerator, the desired product, tert-butyl p-methylthiophenyl carbonate was obtained in a crystalline form. The amount was 112.68 g (yield 94%).

Melting point: 54.5°–55.5° C.

$^1$H-NMR (CDCl$_3$) δ=1.55 (9H, s, t-Bu) (Bu:butyl), 2.42 (3H, s, S-Me), 6.95–7.40 (4H, m,

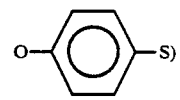

IR (KBr): 1750 cm$^{-1}$ (C=O)
Elemental Analysis:

| | Calculated | Found |
|---|---|---|
| C | 59.97% | 59.49% |
| H | 6.71% | 6.65% |

EXAMPLE 7

To 2.40 g(10 mmol) of tert-butyl p-methylthiophenyl carbonate obtained in Example 6 and 1.38 g (10 mmol) of potassium carbonate were added 10 ml of acetonitrile and then 12.61 g (100 mmol) of dimethyl sulfate. The resulting mixture was stirred for 2 hours at 60° C.

The reaction mixture was cooled to room temperature, and potassium carbonate was removed by filtration. This potassium carbonate was washed with a small amount of acetonitrile. The acetonitrile used for washing was combined with the above filtrate. To the resulting mixture was added ether as a poor solvent to crystallize the sulfonium compound.

A nuclear magnetic resonance (NMR) spectral analysis showed that the product was tert-butyl p-dimethylsulfoniophenyl carbonate methylsulfate having a purity of more than 99%. The amount of the product was 3.55 g and the yield was 97%.

Melting Point: 118°–121° C. (decomposition)

$^1$H-NMR (CDCl$_3$) δ=1.54 (9H, s, t-Bu), 3.43 (6H, s, +SMe$_2$), 3.66 (3H, s, MeSO$_4$$^-$), 7.39, 8.17 (4H, each d, J=10 Hz,

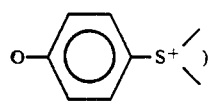

IR (KBr): 1760 cm$^{-1}$ (C=0)
Elemental Analysis

|  | C (%) | H (%) |
|---|---|---|
| Calculated | 45.89 | 6.05 |
| Found | 45.68 | 6.00 |

APPLICATION EXAMPLE 1

(Protection of Amino Group with Water-Soluble Protective Reagent)

Zero point seven five gram (10 mmol) of glycine and 1.52 g (15 mmol) of triethylamine were added to 20 ml of water, and dissolved therein at room temperature. To the solution thus obtained was gradually added 4.40 g (12 mmol) of the tert-butyl p-dimethylsulfoniophenyl carbonate methylsulfate synthesized in Examples 7, and the mixture was stirred for 8 hours at room temperature. The reaction mixture was adjusted to pH 1-2 with citric acid, and the precipitated product was extracted with ethyl acetate. The organic layer was washed three times with water and then dried over sodium sulfate. After drying, the organic layer was concentrated under reduced pressure, and petroleum ether was added thereto to crystallize the product. The product was N-(tert-butyloxycarbonyl)glycine, and the amount was 1.73 g (yield 99%).

Melting Point: 86.5°-89° C. (m.p. reported in the literature: 87°-89° C.)

APPLICATION EXAMPLE 2

(Preparation of Oil-Soluble Protective Reagent)

Fourteen point four two grams (60 mmol) of tert-butyl p-methylthiophenyl carbonate prepared in Example 6 was dissolved in 100 ml of acetone, and 100 g (1.03 mol) of 35% hydrogen peroxide was added thereto while cooling with ice. Then the resulting mixture was stirred at room temperature for 12 hours. After completion of the reaction, the reaction mixture was introduced in 500 ml of water and extracted with 300 ml of ethyl acetate. The organic layer was washed with water, a 5% aqueous sodium hydrogencarbonate solution, and water in this order. After washing, the organic layer was dried over anhydrous sodium sulfate, and ethyl acetate was distilled away under reduced pressure. To the residue thus obtained, methanol was added, and the resulting mixture was allowed to stand in a refrigerator to obtain crystal. The crystal was tert-butyl p-methylsulfonylphenyl carbonate. The amount was 15.61 g (yield 96%).

Melting point: 105.0°-107.0° C.

$^1$H-NMR (CDCl$_3$): δ=1.56 (9H, s, t-Bu), 3.02 (3H, s, SO$_2$Me), 7.36 7.94 (4H), (each d, J=9 Hz,

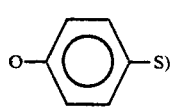

IR (KBr): 1745 cm$^{-1}$ (C=0)
Elemental Analysis:

|  | Calculated | Found |
|---|---|---|
| C | 52.93% | 52.83% |
| H | 5.92% | 5.98% |

APPLICATION EXAMPLE 3

(Protection of Amino Group with Oil-Soluble Protective Reagent)

Four point nine one grams (20 mmol) of N$^{Im}$-benzylhistidine was dissolved in 20 ml of a 4N aqueous sodium hydroxide solution, and a solution of 6.54 g (24 mmol) of tert-butyl p-methylsulfonylphenyl carbonate in 20 ml of dioxane, as prepared in Application Example 2 was added thereto at room temperature. The resulting mixture was stirred for 8 hours. After completion of the reaction, the reaction solution was cooled with ice, and adjusted to pH 2 with 1N hydrochloric acid. This solution was extracted three times with ethyl acetate to remove unreacted protective reagent and p-methylsulfonylphenol. The aqueous layer separated was neutralized with a 1N aqeuous sodium hydroxide solution.

This aqueous layer was concentrated to dryness under reduced pressure and again dissolved in 50 ml of water. The resulting solution was adjusted to pH 5.4 with acetic acid, and on allowing the solution to stand in a refrigerator, the desired product, N-(tert-butyloxycarbonyl)-N$^{Im}$-benzylhistidine was obtained in a crystal form. The amount of the desired product was 6.15 g (yield 89%).

Melting Point: 179°-182° C. (180°-182° C. in the literature)

COMPARATIVE EXAMPLE 3

The procedure of Example 7 was repeated with the exception that potassium carbonate was not used. The amount of the sulfonuim compound obtained was 2.99 g. An NMR analysis showed that the sulfonuim compound was a 33:67 (mol/mol) mixture of tert-butyl p-dimethylsulfoniophenyl carbonate methylsulfate and p-dimethylsulfoniophenol methylsulfate. The yields of butyl p-dimethylsulfoniophenyl carbonate methylsulfate and p-dimethylsulfoniophenol methylsulfate were 33% and 67%, respectively.

EXAMPLES 8 TO 14

The procedure of Example 7 was repeated with the exception that each inorganic compound shown in Table 3 was used in place of potassium carbonate. The results are shown in Table 3. All the inorganic compounds used were in a powder form, and the amount of the inorganic compound used was 10 mmol except for the case of sodium hydrogencarbonate in which the amount was 20 mmol.

TABLE 3

| Example No. | (Type of Inorganic Compound) Inorganic Compound | Yield (%) |
|---|---|---|
| Example 8 | Sodium carbonate (Na$_2$CO$_3$) | 100 |
| Example 9 | Sodium hydrogencarbonate (NaHCO$_3$) | 100 |
| Example 10 | Calcium hydroxide (Ca(OH)$_2$) | 97 |
| Example 11 | Calcium carbonate (CaCO$_3$) | 95 |
| Example 12 | Calcium oxide (CaO) | 99 |
| Example 13 | Magnesium oxide (MgO) | 100 |

TABLE 3-continued (Type of Inorganic Compound)

| Example No. | Inorganic Compound | Yield (%) |
|---|---|---|
| Example 14 | Zinc oxide (ZnO) | 91 |

EXAMPLES 15 TO 18

The procedure of Example 7 was repeated with the exception that sodium carbonate in the amount shown in Table 4 was used in place of potassium carbonate. The results are shown in Table 4.

TABLE 4

(Amount of Inorganic Compound added)

| Example No. | $Na_2CO_3$ (mmol) | $(CH_3)_2SO_4$ (mmol) | Ratio | Yield (%) |
|---|---|---|---|---|
| Example 15 | 0.5 | 100 | 0.005 | 70 |
| Example 16 | 1.0 | 100 | 0.01 | 80 |
| Example 17 | 5.0 | 100 | 0.05 | 91 |
| Example 18 | 50.0 | 100 | 0.5 | 100 |

EXAMPLE 19

Two point four grams (10 mmol) of tert-butyl p-methylthiophenyl carbonate, 1.38 g (10 mmol) of potassium carbonate, and 12.61 g (100 mmol) of dimethyl sulfate were mixed and stirred for 2 hours at 60° C. in the absence of a solvent.

Upon cooling of the reaction mixture to room temperature, the product precipitated, and 10 ml of acetonitrile was added thereto to dissolve the precipitated product. The resulting solution was filtered to remove potassium carbonate, and this potassium carbonate was washed with a small amount of acetonitrile. The acetonitrile used for washing and the filtrate obtained above were combined together, and ether as a poor solvent was added thereto to crystallize the sulfonium compound.

The product was tert-butyl p-dimethylsulfoniophenyl carbonate methylsulfate, and the amount was 3.47 g (yield 95%).

EXAMPLES 20 AND 21

The procedure of Example 7 was repeated with the exception that calcium oxide was used in place of potassium carbonate, and the reaction was carried out at the temperature shown in Table 5. The results are shown in Table 5.

TABLE 5

(Reaction Temperature)

| Example No. | Reaction Temperature (°C.) | Reaction Time (hrs) | Yield (%) |
|---|---|---|---|
| Example 20 | 75 | 2 | 80 |
| Example 21 | 40 | 26 | 82 |

EXAMPLE 22

To 2.40 g (10 mmol) of tert-butyl p-methylthiophenyl carbonate and 0.56 g (10 mmol) of calcium oxide were added 10 ml of acetonitrile and then 1.26 g (10 mmol) of dimethyl sulfate. The resulting mixture was stirred for 20 hours at 60° C.

The reaction mixture was cooled to room temperature, and calcium oxide was removed by filtration. This calcium oxide was washed with a small amount of acetonitrile, and the acetonitrile used for washing and the above filtrate were combined together. To the resulting mixture was added ether as a poor solvent to crystallize the sulfonium compound.

The product was tert-buty p-dimethylsulfoniophenyl carbonate methylsulfate, and the amount was 2.27 g (yield 62%).

COMPARATIVE EXAMPLE 4

The procedure of Example 22 was repeated with the exception that calcium oxide was not used. As a result, tert-butyl p-dimethylsulfoniophenyl carbonate methylsulfate was not almost formed, and only the decomposed product, p-dimethylsulfoniophenol methylsulfate was formed.

EXAMPLE 23

To 1.52 g (5.0 mmol) of p-methoxybenzyl p-methylthiophenyl carbonate and 0.69 g (5.0 mmol) of potassium carbonate were added 5 ml of acetonitrile and then 6.31 g (50 mmol) of dimethyl sulfate. The resulting mixture was stirred for 3 hours at 60° C.

The reaction mixture was cooled to room temperature and potassium carbonate was removed by filtration. This potassium carbonate was washed with a small amount of acetonitrile, and the acetonitrile used for washing was combined together with the above filtrate. To the resulting mixture was added ethyl acetate as a poor solvent to crystallize the sulfonium compound.

The product was p-methoxybenzyl p-dimethylsulfoniophenyl carbonate methylsulfate, and the amount was 2.08 g (yield 97%).

Melting Point: 106°–108° C.

$^1$H-NMR (DMSO-$d_6$): $\delta = 3.27$ (6H, s, $S(CH_3)_2$), 3.37 (3H, s, $CH_3SO_4^-$), 3.76 (3H, s, —$OCH_3$), 5.22 (2H, s, —$CH_2O$—), (each d, J=9,0 Hz,

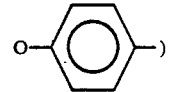

7.61, 8.13 (4H), (each d, J=9.0 Hz,

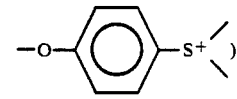

IR (KBr): 1750 cm$^{-1}$ (C=O)
Elemental Analysis

| | C (%) | H (%) |
|---|---|---|
| Calculated | 50.22 | 5.15 |
| Found | 49.73 | 5.24 |

EXAMPLE 24

To 2.54 g (10 mmol) of tert-amyl p-methylthiophenyl carbonate and 1.38 g (10 mmol) of potassium carbonate were added 10 ml of acetonitrile and then 12.61 g (100 mmol) of dimentyl sulfate. The resulting mixture was stirred for 2 hours at 60° C.

The reaction mixture was cooled to room temperature, and potassium carbonate was removed by filtration. This potassium carbonate was washed with a small amount of acetonitrile, and the acetonitrile used for washing was combined together with the above filtrate. To the solution thus obtained was added ether as a poor solvent to crystallize the sulfonium compound.

The product was tert-amyl p-dimethylsulfoniophenyl carbonate methylsulfate, and the amount was 3.50 g (yield 92%).

Melting Point: 92.5°-93.5° C. (decomposition)

$^1$H-NMR (CDCl$_3$): δ=0.98 (3H, t, J=7.4 Hz, tert-Amyl, 1.54 (6H, s, tert-Amyl), 1.87 (2H, q, J=7.4 Hz, tert-Amyl), 3.44 (6H, s, +S(CH$_3$)$_2$), 3.69 (3H, s, CH$_3$SO$_4$−), 7.48 (2H, d, J=9 Hz,

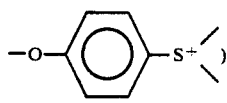

8.20 (2H, d, J=9 Hz,

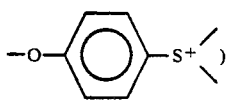

IR (KBr): 1760 cm$^{-1}$ (C=O)
Elemental Analysis

|  | C (%) | H (%) |
|---|---|---|
| Calculated | 47.35 | 6.36 |
| Found | 47.19 | 6.62 |

EXAMPLE 25

Two point eight four grams (10 mmol) of 2-(trimethylsilyl)ethyl p-methylthiophenyl carbonate, 0.56 g (10 mmol) of calcium oxide, and 12.61 g (100 mmol) of dimehtyl sulfate were placed in a flask, and 10 ml of acetonitrile was added thereto. The resulting mixture was stirred for 4 hours at 60° C.

The reaction mixture was cooled to room temperature, and calcium oxide was removed by filtration. This calcium oxide was washed with a small amount of acetonitrile, and the acetonitrile used for washing was combined together with above filtrate. To the resulting mixture was added ether as a poor solvent to crystallize the sulfonium compound.

The product was 2-(trimethylsilyl)ethyl p-dimethylsulfoniophenyl carbonate, and the amount was 4.06 g (yield 99%).

Melting Point: 125°-128° C. (decomposition)

$^1$H-NMR (CDCl$_3$): δ=0.09 (9H, s, Me$_3$Si), 0.95 to 1.35 (2H, m, Si-CH$_2$), 3.43 (6H, s, +SMe$_2$), 3.65 (3H, s, MeSO$_4$−), 4.20 to 4.60 (2H, m, CH$_2$—O—), 7.46, 8.21 (4H), (each d, J=9 Hz,

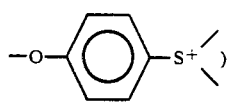

IR (KBr): 1765 cm$^{-1}$ (C=O)
Elemental Analysis

|  | C (%) | H (%) |
|---|---|---|
| Calculated | 43.88 | 6.38 |
| Found | 43.59 | 6.55 |

EXAMPLE 26

Three point one eight grams (10 mmol) of 1-adamantyl p-methylthiophenyl carbonate, 0.56 g (10 mmol) of calcium oxide, and 12.61 g (100 mmol) of dimethyl sulfate were placed in a flask, and 10 ml of acetonitrile was added thereto. The resulting mixture was stirred for 4 hours at 60° C.

The reaction mixture was cooled to room temperature, and calcium oxide was removed by filtration. This calcium oxide was washed with a small amount of acetonitrile, and the acetonitrile used for washing was combined with the above filtrate. To the resulting mixture was added ether as a poor solvent to crystallize the sulfonium compound.

The product was 1-adamantyl p-dimethylsulfoniopheyl carbonate methylsulfate, and the amount was 4.41 g (yield 99%).

Melting Point: 121°-127° C. (decomposition)

$^1$H-NMR (CDCl$_3$): δ=1.69 (6H, s, (broad), adamantyl), 2.17 (9H, s, (broad), adamantyl), 3.42 (6H, s, +SMe$_2$), 3.68 (3H, s, MeSO$_4$−), 7.48, 8.22 (4H), (each d, J=9 Hz,

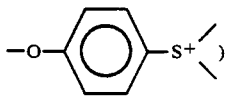

IR (KBr): 1740 cm$^{-1}$ (C=O)
Elemental Analysis

|  | C (%) | H (%) |
|---|---|---|
| Calculated | 54.03 | 6.35 |
| Found | 53.78 | 6.40 |

EXAMPLE 27

Three point two grams (10 mmol) of bornyl p-methylthiophenyl carbonate containing 20% of an isobornyl isomer, 0.56 g (10 mmol) of calcium carbonate, and 12.61 g (100 mmol) of dimethyl sulfate were placed in a flask, and 10 ml of acetonitrile was added thereto. The resulting mixture was stirred for 4 hours at 60° C.

The reaction mixture was cooled to room temperature, and calcium oxide was removed by filtration. This calcium oxide was washed with a small amount of acetonitrile, and the acetonitrile used for washing was combined with the above filtrate. To the resulting mixture was added ether as a poor solvent to crystallize the sulfonium compound.

The product was bornyl p-dimethylsulfoniophenyl carbonate methylsulfate containing 20% of an isobornyl isomer, and the amount was 4.09 g (yield 92%).

Melting Point: 120°–125° C. (decompsition)

$^1$H-NMR (CDCl$_3$) δ=0.92 (9H, s, CH$_3$-C< in bornyl, 1.15 to 2.80 (7H, m, bornyl, 3.41 (6H, s, +SMe$_2$), 3.62 (3H, s, MeSO$_4^-$), 4.50-5.50 (1H, m, >CH—O—), (δ=4.50–4.70: isobornyl), (δ=4.70-5.05: bornyl), 7.46, 8.20 (4H), (each d, J=9 Hz,

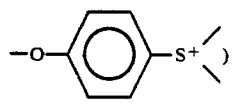

IR (KBr): 1745 cm$^{-1}$ (C=O)
Elemental Analysis

|  | C (%) | H (%) |
|---|---|---|
| Calculated | 63.79 | 6.77 |
| Found | 53.49 | 6.76 |

EXAMPLE 28

Four point eight one grams (20 mmol) of tert-butyl p-methylthiophenyl carbonate, 3.36 g (60 mmol) of calcium oxide, and 30.84 g (200 mmol) of diethyl sulfate were placed in a flask, and 20 ml of acetonitrile was added thereto. The resulting mixture was stirred for 24 hours at 60° C.

The reaction mixture was cooled to room temperature, and calcium oxide was removed by filtration. This calcium oxide was washed with a small amount of acetonitrile, and the acetonitrile for washing was combined with the above filtrate. To the resulting mixture was added ether as a poor solvent to crystallize the sulfonium compound.

The product was tert-butyl p-(S-methyl-S-ethyl)sulfoniophenyl carbonate ethylsulfate, and the amount was 4.16 g (yield 53%).

Melting Point: 105°–110° C. (decomposition)

$^1$H-NMR: δ=1.13 (3H, t, J=7 Hz, CH$_3$CH$_2$—S$^+$), (DNSO-d$_6$), 1.23 (3H, t, J=7 Hz, CH$_3$CH$_2$SO$_4$—), 1.52 (9H, s, tert-Bu), 3.36 (3H, s, CH$_3$—S$^+$), 3.73 (2H, q, J=7 Hz, CH$_3$CH$_2$—S$^+$), 3.80 (2H, q, J=7 Hz, CH$_3$CH$_2$SO$_4^-$), 7.61, 8.20 (4H), (each d, J=9 Hz,

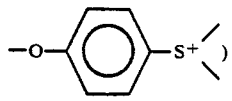

IR (KBr): 1755 cm$^{-1}$ (C=O)
Elemental Analysis

|  | C (%) | H (%) |
|---|---|---|
| Calculated | 48.71 | 6.64 |
| Found | 48.51 | 6.69 |

EXAMPLE 29

Six point zero nine grams (20 mmol) of p-methoxybenzyl p-methylthiophenyl carbonate, 3.36 g (60 mmol) of calcium oxide, and 30.84 g (200 mmol) of diethyl sulfate were placed in a flask, and 20 ml of acetonitrile was added thereto. The resulting mixture was stirred for 24 hours at 60° C.

The reaction mixture was cooled to room temperature, and calcium oxide was removed by filtration. This calcium oxide was washed with a small amount of acetonitrile, and the acetonitrile used for washing was combined with the above filtrate. To the resulting mixture was added ether as a poor solvent to crystallize the sulfonium compound.

The product was p-methoxybenzyl p-(S-methyl-S-ethyl)sulfoniophenyl carbonate ethylsulfate, and the amount was 5.10 g (yield 58%).

Melting Point: 61°–63° C.

$^1$H-NMR: δ=1.18 (3H, t, J=7 Hz, CH$_3$CH$_2$—S$^+$), (DMSO-d$_6$), 1.25 (3H, t, J=7 Hz, CH$_3$CH$_2$SO$_4^-$), 3.42 (3H, s, CH$_3$—S$^+$), 3.57 to 4.08 (7H, m, CH$_3$CH$_2$—S$^+$, CH$_3$CH$_2$SO$_4^-$,

CH$_3$—O (δ=3.80, s)), 5.28 (2H, s, —CH$_2$—O), 6.98, 7.45 (4H), (each d, J=9 Hz,

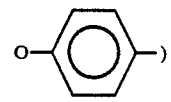

7.66, 8.25 (4H), (each d, J-9 Hz,

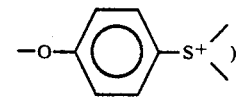

IR (KBr): 1740 cm$^{-1}$ (C=O)
Elemental Analysis

|  | C (%) | H (%) |
|---|---|---|
| Calculated | 54.28 | 5.92 |
| Found | 54.24 | 5.96 |

What is claimed is:

1. A process for producing a sulfonium compound represented by the general formula (III) which comprises reacting an alkylthiophenol derivative represented by the general formula (I) and dialkyl sulfate represented by the general formula (II) in the presence of at least one inorganic compound selected from alkali metal carbonate, alkali metal hydrogencarbonate, alkaline earth metal hydroxide, alkaline earth metal carbonate, and oxides of Group II metals of the Periodic Table, General Formula (I):

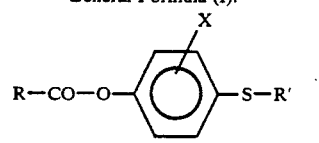

General Formula (II):
(R$^2$)$_2$SO$_4$

General Formula (III):

-continued

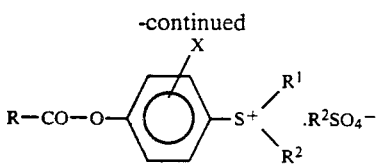

Wherein $R^1$ and $R^2$ may be identical or different and are each an alkyl group having 1 to 4 carbon atoms, X is a hydrogen atom, a halogen atom, or an alkyl group having 1 to 4 carbon atoms, and R is a tert-butyloxy group, a tert-amyloxy group, a p-methoxybenzyloxy group, a 2-(trimethylsilyl)ethoxy group, a 1-adamantyloxy group, a bornyloxy group, or an isobornyloxy group.

2. The process as claimed in claim 1, wherein the inorganic compound is at least one compound selected from sodium carbonate, potassium carbonate, calcium carbonate, sodium hydrogencarbonate, calcium hydroxide, calcium oxide, magnesium oxide, and zinc oxide.

3. The process as claimed in claim 1, wherein the alkylthiophenol derivative represented by the general formula (I) is at least one compound selected from tert-butyl p-methylthiophenyl carbonate, p-methoxybenzyl p-methylthiophenyl carbonate, tert-amyl p-methylthiophenyl carbonate, 2-(trimethylsilyl)ethyl p-methylthiophenyl carbonate, 1-adamantyl p-methylthiophenyl carbonate, and bornyl p-methylthiophenyl carbonate.

4. The process as claimed in claim 1, wherein the dialkyl sulfate represented by the general formula (II) is dimethyl sulfate or diethyl sulfate.

5. The process as claimed in claim 1, wherein the amount of the dialkyl sulfate is 1 to 15 mol per mol of the alkylthiophenol derivative represented by the general formula (I).

6. The process as claimed in claim 1, wherein the amount of the inorganic compound is 0.01 to 1 equivalent per dialkyl sulfate.

7. The process as claimed in claim 1, wherein the reaction is carried out in the presence of a solvent.

8. The process as claimed in claim 7, wherein the solvent is at least one compound selected from the group consisting of aprotic polar solvents, esters, ethers, and aromatic hydrocarbons.

9. The process as claimed in claim 7, wherein the solvent is at least one compound selected from the group consisting of acetonitrile, ethyl acetate, and dioxane.

10. The process as claimed in claim 7, wherein the amount of the solvent is 0.1 to 10 liters per mol of the alkylthiophenol derivative of the general formula (I).

* * * * *